United States Patent [19]
Boudreau

[11] Patent Number: 5,837,000
[45] Date of Patent: Nov. 17, 1998

[54] TANNING SCREEN

[76] Inventor: Jerome Boudreau, 262 E. Beaudoin, Bourbonnais, Ill. 60914

[21] Appl. No.: 974,753
[22] Filed: Nov. 19, 1997
[51] Int. Cl.[6] .................................................. A61N 33/00
[52] U.S. Cl. ................................. 607/95; 607/81; 607/88
[58] Field of Search .................................. 607/81, 88, 95; 160/135

[56] References Cited

U.S. PATENT DOCUMENTS

| 2,078,975 | 5/1937 | Roberts | 607/95 |
|---|---|---|---|
| 2,981,256 | 4/1961 | Besnah | 607/95 |
| 3,023,753 | 3/1962 | Wheless | 607/95 |
| 3,498,587 | 3/1970 | Friedberg | 607/95 |
| 3,610,249 | 10/1971 | Baker | 607/95 |
| 3,670,750 | 6/1972 | Johnston | 607/95 |
| 5,085,212 | 2/1992 | DeCosta | 607/95 |

Primary Examiner—Jennifer Bahr
Assistant Examiner—Roy D. Gibson

[57] ABSTRACT

A new tanning screen for providing a portable and foldable device for reflecting sunlight towards a user. The inventive device includes a frame member having a rectangular end wall frame portion, a U-shaped first side wall frame portion, and a U-shaped second side wall frame portion. The side wall frame portions each have a pair of horizontal arms that are each pivotally coupled to one of the four mounting arms of the end wall frame portion. Each horizontal arm has proximal and distal extension portions that are pivotally coupled to one another. An elongate rectangular panel member is mounted to the frame member such that the panel member substantially covers the frame member. The panel member includes a light reflective surface for helping direct light towards a user for tanning.

4 Claims, 2 Drawing Sheets

TANNING SCREEN

BACKGROUND OF THE INVENTION

1. Field of the Invention

The present invention relates to tanning and screening devices and more particularly pertains to a new tanning screen for providing a portable and foldable device for reflecting sunlight towards a user.

2. Description of the Prior Art

The use of tanning and screening devices is known in the prior art. More specifically, tanning and screening devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art tanning and screening devices include U.S. Pat. No. 5,085,212; U.S. Pat. No. 4,856,520; U.S. Pat. No. Des. 314,429; U.S. Pat. No. 5,088,514; and U.S. Pat. No. 4,981,152.

While these devices fulfill their respective, particular objectives and requirements, the aforementioned patents do not disclose a new tanning screen. The inventive device includes a frame member having a rectangular end wall frame portion, a U-shaped first side wall frame portion, and a U-shaped second side wall frame portion. The side wall frame portions each have a pair of horizontal arms that are each pivotally coupled to one of the four mounting arms of the end wall frame portion. Each horizontal arm has proximal and distal extension portions that are pivotally coupled to one another. An elongate rectangular panel member is mounted to the frame member such that the panel member substantially covers the frame member. The panel member includes a light reflective surface for helping direct light towards a user for tanning.

In these respects, the tanning screen according to the present invention substantially departs from the conventional concepts and designs of the prior art, and in so doing provides an apparatus primarily developed for the purpose of providing a portable and foldable device for reflecting sunlight towards a user.

SUMMARY OF THE INVENTION

In view of the foregoing disadvantages inherent in the known types of tanning and screening devices now present in the prior art, the present invention provides a new tanning screen construction wherein the same can be utilized for providing a portable and foldable device for reflecting sunlight towards a user.

The general purpose of the present invention, which will be described subsequently in greater detail, is to provide a new tanning screen apparatus and method which has many of the advantages of the tanning and screening devices mentioned heretofore and many novel features that result in a new tanning screen which is not anticipated, rendered obvious, suggested, or even implied by any of the prior art tanning and screening devices, either alone or in any combination thereof.

To attain this, the present invention generally comprises a frame member having a rectangular end wall frame portion, a U-shaped first side wall frame portion, and a U-shaped second side wall frame portion. The side wall frame portions each have a pair of horizontal arms that are each pivotally coupled to one of the four mounting arms of the end wall frame portion. Each horizontal arm has proximal and distal extension portions that are pivotally coupled to one another. An elongate rectangular panel member is mounted to the frame member such that the panel member substantially covers the frame member. The panel member includes a light reflective surface for helping direct light towards a user for tanning.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new tanning screen apparatus and method which has many of the advantages of the tanning and screening devices mentioned heretofore and many novel features that result in a new tanning screen which is not anticipated, rendered obvious, suggested, or even implied by any of the prior art tanning and screening devices, either alone or in any combination thereof.

It is another object of the present invention to provide a new tanning screen which may be easily and efficiently manufactured and marketed.

It is a further object of the present invention to provide a new tanning screen which is of a durable and reliable construction.

An even further object of the present invention is to provide a new tanning screen which is susceptible of a low cost of manufacture with regard to both materials and labor, and which accordingly is then susceptible of low prices of sale to the consuming public, thereby making such tanning screen economically available to the buying public.

Still yet another object of the present invention is to provide a new tanning screen which provides in the apparatuses and methods of the prior art some of the advantages thereof, while simultaneously overcoming some of the disadvantages normally associated therewith.

Still another object of the present invention is to provide a new tanning screen for providing a portable and foldable device for reflecting sunlight towards a user.

Yet another object of the present invention is to provide a new tanning screen which includes a frame member having a rectangular end wall frame portion, a U-shaped first side wall frame portion, and a U-shaped second side wall frame portion. The side wall frame portions each have a pair of horizontal arms that are each pivotally coupled to one of the four mounting arms of the end wall frame portion. Each horizontal arm has proximal and distal extension portions that are pivotally coupled to one another. An elongate rectangular panel member is mounted to the frame member such that the panel member substantially covers the frame member. The panel member includes a light reflective surface for helping direct light towards a user for tanning.

Still yet another object of the present invention is to provide a new tanning screen that helps direct sunlight towards a user while helping to shelter a user from blowing wind.

Even still another object of the present invention is to provide a new tanning screen that helps a user to suntan all year round.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
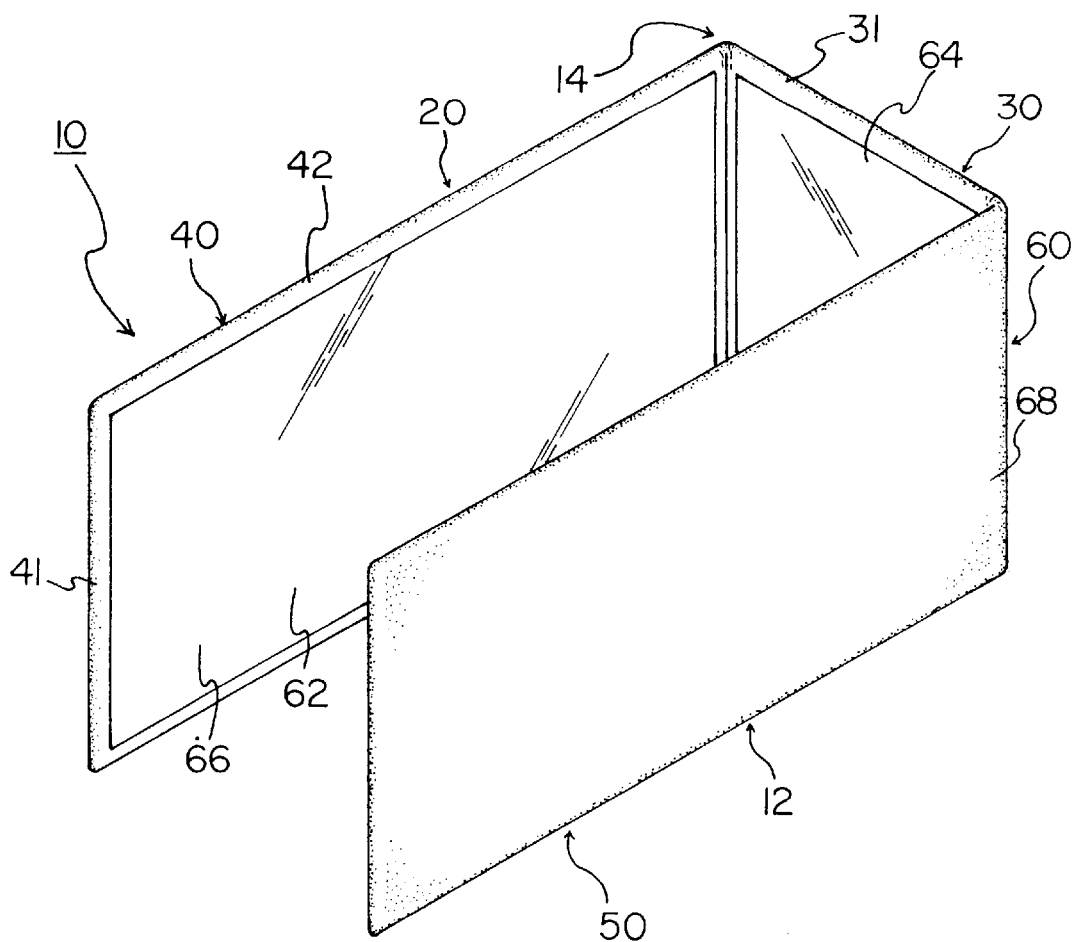
FIG. 1 is a schematic perspective view of a new tanning screen according to the present invention in an open and extended position.
Figure 2:
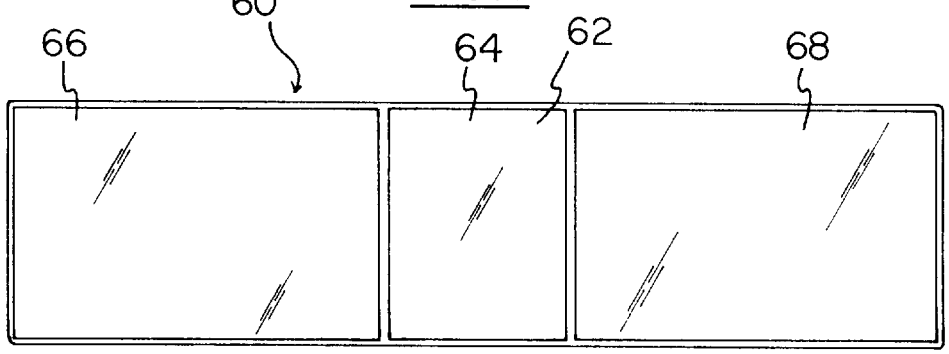
FIG. 2 is a schematic side view of the panel member of the present invention.

With reference now to the drawings, and in particular to FIGS. 1 through 4 thereof, a new tanning screen embodying the principles and concepts of the present invention and generally designated by the reference numeral 10 will be described.

As best illustrated in FIGS. 1 through 4, the tanning screen 10 generally comprises a frame member 20 having a rectangular end wall frame portion 30, a U-shaped first side wall frame portion 40, and a U-shaped second side wall frame portion 50. The side wall frame portions 40,50 each have a pair of horizontal arms 42,43,52,53 that are each pivotally coupled to one of the four mounting arms 36 of the end wall frame portion 30. Each horizontal arm 42,43,52,53 has proximal and distal extension portions 46,48,56,58 that are pivotally coupled to one another. An elongate rectangular panel member 60 is mounted to the frame member 20 such that the panel member 60 substantially covers the frame member 20. The panel member 60 includes a light reflective surface 62 for helping direct light towards a user for tanning.

The end wall frame portion 30 has a pair of spaced apart and substantially parallel elongate horizontal tubes 31,32 each having a pair of opposite ends. The horizontal tubes 31,32 are connected by a pair of spaced apart and substantially parallel elongate vertical tubes 33,34 extending therebetween so that the tubes 31,32,33,34 are substantially coplanar. At the ends of each horizontal tube 31,32 is one of the mounting arms 36 extending substantially perpendicular to the longitudinal axis of its respective the horizontal tube 31,32.

Each of the side wall frame portions 40,50 has a pair of spaced apart and substantially parallel elongate horizontal arms 42,43,52,53, and a vertical cross arm 41,51. Each of the horizontal arms 42,43,52,53 has a terminal end 44,54 and elongate proximal and distal extension portions 46,48,56,58. The proximal extension portions 46,56 of each side wall frame portion horizontal arms 42,43,52,53 are connected together by their respective vertical cross arms 41,51 extending therebetween.

Figure 3:
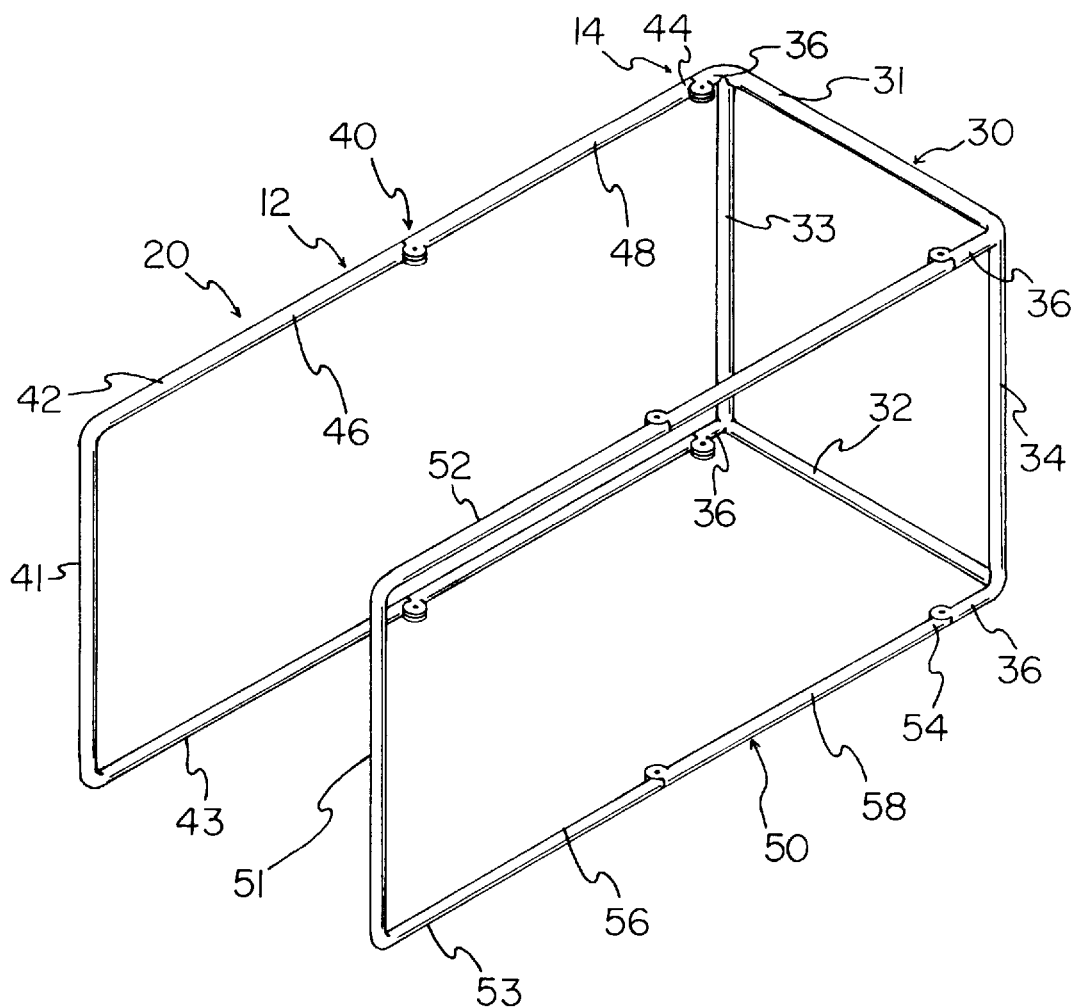
FIG. 3 is a schematic perspective view of the frame member of the present invention in an open and extended position.
Figure 4:
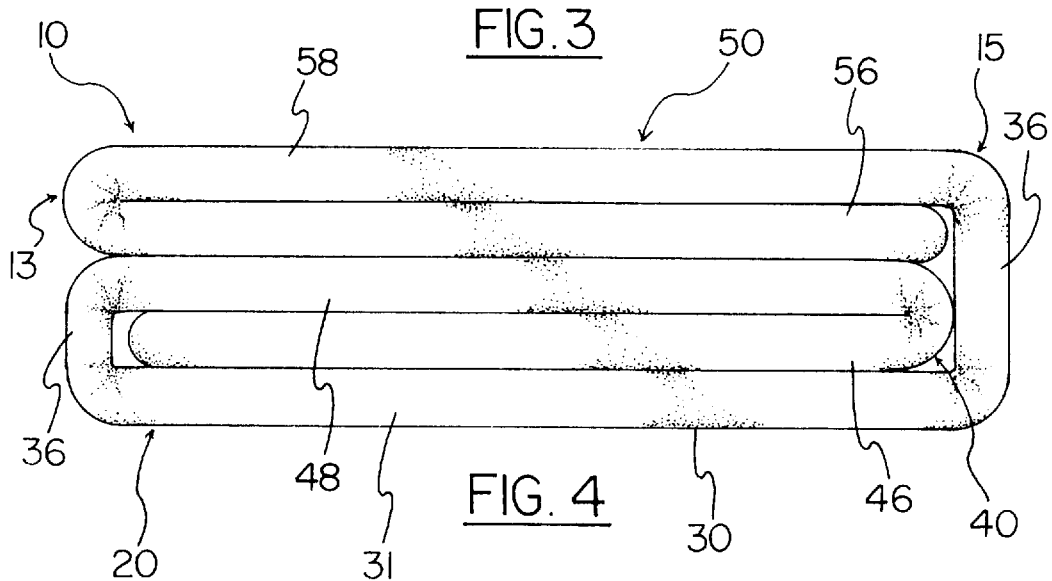
FIG. 4 is a schematic top side view of the present invention in a closed and folded position.

The proximal and distal extension portions 46,48,56,58 of each side wall frame portion horizontal arm 42,43,52,53 are pivotally coupled to one another. This permits each proximal and distal extension portion 46,48,56,58 of each side wall frame portion horizontal arm 42,43,52,53 to be pivotable between an extended position 12, as shown in FIG. 3, and a folded position 13, as shown in FIG. 4. As shown in FIG. 3, the horizontal arms and the vertical cross arm of each side wall frame portion are substantially coplanar when the proximal and distal extension portions of the side wall frame portion horizontal arms are in the extended position 12. As shown in FIG. 4, the vertical cross arm of each side wall frame portion is positioned adjacent the end wall frame portion 30 when the proximal and distal extension portions of the side wall frame portion horizontal arms are in the folded position.

With reference to FIG. 3, the terminal ends 44,54 are pivotally coupled to the mounting arms 36 of the end wall frame portion 30. This arrangement permits each side wall frame portion 40,50 to be pivotable between an open position 14 and a closed position 15 with respect to the end wall frame portion.

As shown in FIG. 3, the open position 14 of each side wall frame portion 40,50 is characterized by the side wall frame portion 40,50 being extended substantially perpendicular from the end wall frame portion 30. Preferably, the first side wall frame portion 40 faces the second side wall frame portion 50 when the side wall frame portions 40,50 are positioned in the open position 14. The closed position 15 of each side wall frame portion 40,50 is characterized by the horizontal arm 42,42,52,53 of the side wall frame portions 40,50 being substantially parallel to the horizontal tubes 31,32 of the end wall frame portion 30. In this preferred embodiment, with particular reference to FIG. 4, the mounting arms 36 of one side of the end wall frame portion 30 are longer (ideally, twice as long) than the mounting tabs on the other side of the end wall frame portion 30 so that the side wall frame portions 40,50 may be compactly folded up when they are both positioned in the folded and closed position 13,15.

Ideally, the panel member 60 is made from a fabric material to keep the tanning screen light weight. The panel member 60 also has a light reflective surface 62 that permits the directing of light rays towards a user when in use. Any reflective coating know in the art may be used for the light reflective surface 62. Ideally, the light reflective surface 62 comprises an reflective metal such as aluminum. The elongate rectangular panel member 60 preferably has an end wall panel 64 interposed between a pair of side wall panels 66,68. The panel member 60 is mounted to the frame member 20 such that the end wall panel 64 substantially covers the end wall frame portion 30 while each the side wall panels 66,68 substantially covers a corresponding the side wall frame portion 40,50.

In use, the tanning screen 10 is deployed by resting the invention on a ground surface and positioning the horizontal arms 42,43,52,53 of the side wall frame portions 40,50 in the extended and open position 12,14. This permits a user to rest between the two side walls 40,50 so that the user may gain the benefit of the sunlight being reflected off of the panel member light reflective surface 62. Ideally, the vertical members 33,34,41,51 of the frame member 20 are long enough to provide a sufficient amount of reflective light and sufficient wind shelter to a user. An illustrative dimension of the vertical members is about four feet. Illustratively, an ideal dimension for the horizontal arms 42,43,52,53 is about seven feet so that a user may lay between the side walls 40,50 fully extended to obtain the benefit of the most reflected light. Ideally, the vertical tubes 33,34 are about three feet in length to permit a user to comfortably lie or sit between the two side walls 40,50.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A foldable tanning screen, comprising:

a frame member having a rectangular end wall frame portion, a U-shaped shaped first side wall frame portion, and a U-shaped second side wall frame portion;

said end wall portion having four mounting arms being extended therefrom;

said first side wall frame portion having a pair of spaced apart and substantially parallel elongate horizontal arms, and a vertical cross arm;

each of said first side wall frame portion horizontal arms having a terminal end and elongate proximal and distal extension portions with a common length equal to that of the end wall portion, said terminal end of said first side wall frame portion horizontal arms being pivotally coupled to a said mounting arm of said end wall frame portion, said proximal and distal extension portions of each said first side wall frame portion horizontal arm being pivotally coupled to one another, said proximal extension portions of first side wall frame portion horizontal arms being connected together by said first side wall frame portion vertical cross arm extending therebetween;

said second side wall frame portion having a pair of spaced apart and substantially parallel elongate horizontal arms, and a vertical cross arm;

each of said second side wall frame portion horizontal arms having a terminal end and elongate proximal and distal extension portions with a common length equal to that of the end wall portion, said terminal end of said second side wall frame portion horizontal arms being pivotally coupled to a said mounting arm of said end wall frame portion, said proximal and distal extension portions of each said second side wall frame portion horizontal arm being pivotally coupled to one another, said proximal extension portions of second side wall frame portion horizontal arms being connected together by said second side wall frame portion vertical cross arm extending therebetween; and an elongate rectangular panel member being mounted to said frame member such that said panel member substantially covers said frame member, said panel member having a light reflective surface;

wherein said end wall frame portion comprises a pair of spaced apart and substantially parallel elongate horizontal tubes each having a pair of opposite ends, said end wall frame portion horizontal tubes being connected by a pair of spaced apart and substantially parallel elongate vertical tubes being extended between said end wall frame portion horizontal tubes, said end wall frame portion horizontal tubes and said end wall frame portion vertical tubes being substantially coplanar, each said end of said end wall frame portion horizontal tubes having a mounting arm being extended substantially perpendicular to the longitudinal axis of its respective said end wall frame portion horizontal tube and being fixed with respect thereto, wherein a first one of the mounting arms of each end wall frame portion horizontal tube is greater than a second one of the mounting arms of each end wall frame portion horizontal tube;

wherein each said side wall frame portions is pivotable between an open position and a closed position with respect to said end wall frame portion, said open position of each said side wall frame portion being characterized by said side wall frame portion being extended substantially perpendicular from said end wall frame portion, said first side wall frame portion facing said second side wall frame portion when said first and second side wall frame portions are positioned in said open position, said closed position of each said side wall frame portion being characterized by each said horizontal arm of said side wall frame portions being substantially parallel to said horizontal tubes said end wall frame portion.

2. The foldable tanning screen of claim 1, wherein said proximal and distal extension portions of said first side wall frame portion horizontal arms are pivotable between a first extended position and a first folded position, said horizontal arms and said vertical cross arm of said first side wall frame portion being substantially coplanar when said proximal and distal extension portions of said first side wall frame portion horizontal arms are in said first extended position, said vertical cross arm of said first side wall frame portion being positioned adjacent said end wall frame portion when said proximal and distal extension portions of said first side wall frame portion horizontal arms are in said first folded position; and wherein said proximal and distal extension portions of said second side wall frame portion horizontal arms are pivotable between a second extended position and a second folded position, said horizontal arms and said vertical cross arm of said second side wall frame portion being substantially coplanar when said proximal and distal extension portions of said second side wall frame portion horizontal arms are in said second extended position, said vertical cross arm of said second side wall frame portion being positioned adjacent said end wall frame portion when said proximal and distal extension portions of said second side wall frame portion horizontal arms are in said second folded position.

3. The foldable tanning screen of claim 1, wherein said panel member has an end wall panel interposed between a pair of side wall panels, wherein said panel member is mounted to said frame member such that said end wall panel of said panel member substantially covers said end wall frame portion of said frame member and each said side wall panels of said panel member substantially covers a corresponding said side wall frame portion of said frame member.

4. A foldable tanning screen, comprising:

a frame member having a rectangular end wall frame portion, a U-shaped first side wall frame portion, and a U-shaped second side wall frame portion;

said end wall frame portion having a pair of spaced apart and substantially parallel elongate horizontal tubes each having a pair of opposite ends, said end wall frame portion horizontal tubes being connected by a pair of spaced apart and substantially parallel elongate vertical tubes being extended between said end wall frame portion horizontal tubes, said end wall frame portion horizontal tubes and said end wall frame portion vertical tubes being substantially coplanar, each said end of said end wall frame portion horizontal tubes having a mounting arm being extended substantially perpendicular to the longitudinal axis of its respective said end wall frame portion horizontal tube and being fixed with respect thereto, wherein a first one of the mounting arms of each end wall frame portion horizontal tube is greater than a second one of the mounting arms of each end wall frame portion horizontal tube;

said first side wall frame portion having a pair of spaced apart and substantially parallel elongate horizontal arms, and a vertical cross arm;

each of said first side wall frame portion horizontal arms having a terminal end and elongate proximal and distal extension portions with a common length equal to that of the end wall portion, said terminal end of said first side wall frame portion horizontal arms being pivotally coupled to a said mounting arm of said end wall frame portion horizontal tubes, said proximal and distal extension portions of each said first side wall frame portion horizontal arm being pivotally coupled to one another, said proximal extension portions of first side wall frame portion horizontal arms being connected together by said first side wall frame portion vertical cross arm extending therebetween;

wherein said proximal and distal extension portions of said first side wall frame portion horizontal arms are pivotable between a first extended position and a first folded position, said horizontal arms and said vertical cross arm of said first side wall frame portion being substantially coplanar when said proximal and distal extension portions of said first side wall frame portion horizontal arms are in said first extended position, said vertical cross arm of said first side wall frame portion being positioned adjacent said end wall frame portion when said proximal and distal extension portions of said first side wall frame portion horizontal arms are in said first folded position;

said second side wall frame portion having a pair of spaced apart and substantially parallel elongate horizontal arms, and a vertical cross arm;

each of said second side wall frame portion horizontal arms having a terminal end and elongate proximal and distal extension portions with a common length equal to that of the end wall portion, said terminal end of said second side wall frame portion horizontal arms being pivotally coupled to a said mounting arm of said end wall frame portion horizontal tubes, said proximal and distal extension portions of each said second side wall frame portion horizontal arm being pivotally coupled to one another, said proximal extension portions of second side wall frame portion horizontal arms being connected together by said second side wall frame portion vertical cross arm extending therebetween;

wherein said proximal and distal extension portions of said second side wall frame portion horizontal arms are pivotable between a second extended position and a second folded position, said horizontal arms and said vertical cross arm of said second side wall frame portion being substantially coplanar when said proximal and distal extension portions of said second side wall frame portion horizontal arms are in said second extended position, said vertical cross arm of said second side wall frame portion being positioned adjacent said end wall frame portion when said proximal and distal extension portions of said second side wall frame portion horizontal arms are in said second folded position;

wherein each said side wall frame portions are pivotable between an open position and a closed position with respect to said end wall frame portion, said open position of each said side wall frame portion being characterized by said side wall frame portion being extended substantially perpendicular from said end wall frame portion, said first side wall frame portion facing said second side wall frame portion when said first and second side wall frame portions are positioned in said open position, said closed position of each said side wall frame portion being characterized by each said horizontal arm of said side wall frame portions being substantially parallel to said horizontal tubes said end wall frame portion; and an elongate rectangular panel member having an end wall panel interposed between a pair of side wall panels, said panel member being mounted to said frame member such that said end wall panel of said panel member substantially covers said end wall frame portion of said frame member and each said side wall panels of said panel member substantially covers a corresponding said side wall frame portion of said frame member, said panel member having a light reflective surface.

* * * * *